United States Patent [19]

Urano et al.

[11] Patent Number: 5,430,170
[45] Date of Patent: Jul. 4, 1995

[54] PROCESS FOR PREPARING DIALKYL CARBONATES

[75] Inventors: Yoshiaki Urano, Kawasaki; Masaru Kirishiki, Yokohama; Yoshiyuki Onda; Hideaki Tsuneki, both of Tokyo, all of Japan

[73] Assignee: Nippon Shokubai Co., Ltd., Osaka, Japan

[21] Appl. No.: 155,925

[22] Filed: Nov. 23, 1993

[30] Foreign Application Priority Data

Nov. 25, 1992 [JP] Japan .................................. 4-314800
Feb. 17, 1993 [JP] Japan .................................. 5-053025

[51] Int. Cl.6 ............................................. C07C 69/96
[52] U.S. Cl. ....................................................... 558/277
[58] Field of Search ........................................ 558/277

[56] References Cited

U.S. PATENT DOCUMENTS

| | | |
|---|---|---|
| 3,642,858 | 2/1972 | Frevel et al. . |
| 4,062,884 | 12/1977 | Romano et al. . |
| 4,181,676 | 1/1980 | Buysch et al. . |
| 4,307,032 | 12/1981 | Krimm et al. . |
| 4,559,180 | 12/1985 | Green . |
| 4,661,609 | 4/1987 | Knifton .............................. 558/277 |
| 4,681,967 | 7/1987 | Green . |
| 4,691,041 | 9/1987 | Duranleau et al. ................. 558/277 |
| 5,214,182 | 5/1993 | Knifton .............................. 558/277 |

FOREIGN PATENT DOCUMENTS

| | | |
|---|---|---|
| 478073A2 | 4/1992 | European Pat. Off. . |
| 56-10144 | 2/1981 | Japan . |
| 56-40708 | 9/1981 | Japan . |
| 59-106436 | 6/1984 | Japan . |
| 59-28542 | 7/1984 | Japan . |
| 60-22697 | 6/1985 | Japan . |
| 60-22698 | 6/1985 | Japan . |
| 60-27658 | 6/1985 | Japan . |
| 61-4381 | 2/1986 | Japan . |
| 61-5467 | 2/1986 | Japan . |
| 61-16267 | 4/1986 | Japan . |
| 63-41432 | 2/1988 | Japan . |
| 63-238043 | 10/1988 | Japan . |
| 1-31737 | 2/1989 | Japan . |
| 44354 | 2/1991 | Japan . |
| 4-9356 | 1/1992 | Japan . |

Primary Examiner—Mary C. Lee
Assistant Examiner—Michael G. Ambrose
Attorney, Agent, or Firm—Sherman and Shalloway

[57] ABSTRACT

A industrially advantageous process for preparing dialkyl carbonates is provided. The process is characterized in that an alkylene carbonate and an alcohol are subjected to an transesterification in the presence of a catalyst which contains, as the catalytically active component, at least one rare-earth oxide. According to this process, the transesterification progresses rapidly due to the excellent activity of the catalyst, and the catalyst can be readily separated after termination of the reaction, allowing high efficiency isolation and purification of dialkyl carbonate.

18 Claims, No Drawings

PROCESS FOR PREPARING DIALKYL CARBONATES

This invention relates to a process for preparing dialkyl carbonates. More particularly, the invention relates to a process for preparing dialkyl carbonates which are represented by the following general formula (3), through a transesterification between an alkylene carbonate of the following general formula (1) and an alcohol of the following general formula (2), in the presence of a catalyst. In said transesterification, an alkylene glycol of the following general formula (4) also is formed, besides the object dialkyl carbonate.

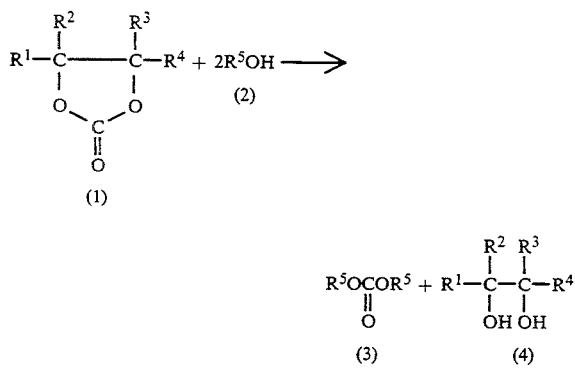

In the above formulae, each of $R^1$, $R^2$, $R^3$ and $R^4$ is independently selected from the group consisting of hydrogen, alkyl, alkenyl, aryl, cycloalkyl, alkoxyalkyl and alkoxy; and $R^5$ is selected from the group consisting of $C_1$–$C_{20}$ alkyl, alkenyl, arylalkyl, cycloalkyl and alkoxyalkyl.

Dialkyl carbonates are the compounds useful for such uses as solvents and gasoline additives. Besides, demands for the same compounds are expected to expand in the future, in the use field of carbonating agent or alkylating agent of high safety and easy handling, which can substitute highly toxic phosgene or dimethyl sulfate.

For preparation of dialkyl carbonates, various methods for carrying out transesterification between an alkylene carbonate and an alcohol have been proposed. The fundamental technology supporting those methods lies in the ester-interchange catalysts which are classified into homogeneous and heterogeneous catalysts.

As such homogeneous catalysts, for example, alkali metals or alkali metal derivatives (U.S. Pat. No. 3,642,858, Japan Kokoku 16267/86), tertiary aliphatic amines (Japan Kokoku 28542/84), alkyltin alkoxides (Japan Kokoku 40708/81), alkoxides of zinc, aluminium or titanium (Japan Kokoku 22697/85), thallium compounds (Japan Kokoku 27658/85), complexes of Lewis acids and nitrogen-containing organic bases (Japan Kokoku 22698/85), phosphine compounds (Japan Kokoku 4381/86), quaternary phosphonium salts (Japan Kokai 10144/81) and Group V-element-containing Lewis bases and epoxides or cyclic amidines (Japan Kokai 106436/84), etc. have been proposed.

The methods using those homogeneous catalysts have the advantage that high catalytic activity is obtained using a small amount of such a catalyst. There is the drawback, however, that separation of the catalyst from the reaction liquid is difficult. Because the transesterification is an equilibrium reaction, in an attempt to isolate the intended dialkyl carbonate by distillation of the reaction liquid without advance separation of the catalyst, the equilibrium is broken during the distillation to induce a reverse reaction. Whereby such a disadvantage is caused that the dialkyl carbonate once formed returns to the starting alkylene carbonate. Furthermore, due to the presence of the catalyst, such side-reactions as decomposition, polymerization, or the like concurrently take place during the distillation, eventually decreasing the efficiency of the purification step. Thus, those methods cannot provide a satisfactory process.

Whereas, heterogeneous catalysts can be readily separated from the reaction liquid, and the methods using them are, therefore, free from the above problems accompanying the homogeneous catalysts.

As such heterogeneous catalysts, ion-exchange resins, in particular, solid, strongly basic anion-exchange resins having quaternary ammonium groups as the exchange group, have been proposed (Japan Kokai 31737/89 and 238043/88). These heterogeneous catalysts exhibit relatively high catalytic activity, but have problems in heat resistance and durability, which make them unfit for industrial use. For instance, there is such a drawback that the quaternary ammonium groups decompose under high temperature conditions to form a nitrogen-containing compound which dissolves into the reaction liquid.

Methods using inorganic solid catalysts as the heterogeneous catalysts have also been proposed. Such catalysts include silica-titania solid acid (Japan Kokoku 5467/86), alkali and alkaline earth silicates impregnated into silica and ammonium exchanged zeolite (Japan Kokai 31737/89), oxides of zirconium, titanium and tin (Japan Kokai 41432/88) and lead compounds (Japan Kokai 9356/92). These methods, however, generally exhibit low catalytic activity and are short for practical use.

Recently, furthermore, methods using hydrotalcite compounds containing MgO and $Al_2O_3$ (Japan Kokai 43354/91) or mixed metal (EP-A-I 478073) as the heterogeneous catalyst have been proposed. While catalytic activity is improved in these proposals over that in the above-recited earlier methods, they are still unsatisfactory because of such problems as that many hours are necessary before the transesterification reaches equilibrium or that high reaction temperature is required.

Accordingly, therefore, an object of the present invention is to solve the problems inherent in the conventional technology for preparation of dialkyl carbonates through a transesterification between alkylene carbonates and alcohols. Another object of the present invention is to provide a process for preparing dialkyl carbonates with industrial advantages, using a solid catalyst excelling in catalytic activity and durability.

After concentrative studies on preparation of dialkyl carbonates through a transesterification between alkylene carbonates and alcohols, we have discovered that the foregoing objects can be achieved by using oxides of rare-earth elements as the catalyst.

Thus, according to the invention provided is a process for preparing dialkyl carbonates of the general formula (3) through a transesterification between an alkylene carbonate expressed by the general formula (1) and an alcohol expressed by the general formula (2), said process being characterized by the use of a catalyst which contains at least one rare-earth oxide as the catalytically active component.

As the alkylene carbonates represented by the general formula (1) which are used as one of the starting materials in the present invention, ethylene carbonate, propylene carbonate, 1,2-butylene carbonate, 2,3-butylene carbonate, 1,2-pentylene carbonate, styrene carbonate, 3-methoxy-1,2-propylene carbonate, 3-ethoxy-1,2-propylene carbonate and the like may be named for example. Their mixtures may also be used. Of these, ethylene carbonate or propylene carbonate are particularly useful industrially, because they are industrially readily available, and the alkylene glycols expressed by the general formula (4), which are side-produced of the reactions using these carbonates, have high utilization value.

Examples of the alcohols to be used as the other starting material in the present invention, which are expressed by the general formula (2), include: methyl alcohol, ethyl alcohol, propyl alcohol, isopropyl alcohol, butyl alcohol, isobutyl alcohol, t-butyl alcohol, pentyl alcohol, hexyl alcohol, octyl alcohol, 2-ethylhexyl alcohol, decyl alcohol, dodecyl alcohol, tetradecyl alcohol, hexadecyl alcohol, octadecyl alcohol, allyl alcohol, benzyl alcohol, cyclohexyl alcohol, ethylene glycol-monomethyl ether, ethylene glycol-monoethyl ether, ethylene glycol-monopropyl ether, ethylene glycol-monobutyl ether, diethylene glycol-monomethyl ether, diethylene glycol-monoethyl ether, etc. Their mixtures may also be used. Of these, methyl alcohol is industrially useful, because dimethyl carbonate which is the dialkyl carbonate prepared therefrom, is of high demand.

The catalyst used in the present invention contains as the catalytically active component, oxide of at least one rare-earth element. The catalyst may also contain oxide or oxides of an element or elements other than rare-earth elements as additional catalytically active component. Specific examples of the rare-earth elements are scandium (Sc), yttrium (Y) and lanthanide (La, Ce, Pr, Nd, Pm, Sm, Eu, Gd, Tb, Dy, Ho, Er, Tm Yb and Lu). While rare-earth elements generally form oxides of an oxidation number 3, oxides of oxidation number 4 or even higher oxidation number, or lower oxides of oxidation numbers less than 3, or mixtures of those oxides, may be used without critical limitation. From the standpoint of easy industrial utilization, those preferred are yttrium oxide, lanthanum oxide, cerium oxide and mixtures of at least two rare-earth oxides.

These oxides of rare-earth elements can be obtained, for example, by calcining oxalates, acetates, nitrates, hydroxides or carbonates of the rare-earth elements in air. Commercially available oxides of rare-earth elements may also be utilized as the catalytic component for the present invention.

Those oxides of rare-earth elements used in the catalyst of the present invention preferably are porous and have large specific surface area, to exhibit higher catalytic activity. The specific surface area normally ranges 5–500 m$^2$/g, preferably 10–300 m$^2$/g. When it is less than 5 m$^2$/g, satisfactory catalytic activity cannot be obtained. Whereas, when it exceeds 500 m$^2$/g, strength of the catalyst is objectionably lowered to cause durability problem.

Those oxides of rare-earth elements are preferably activated by a heat-treatment in an inert gas flow such as of nitrogen before their use as the catalyst, with the view to remove the substances adsorbed onto their surface, such as carbon dioxide or water. The treating temperature in that occasion ranges 100°–1,000° C., more preferably 200°–800° C. The treating temperature lower than 100° C. is objectionable because such achieves insufficient release of the adsorbed matter. Whereas, the treating temperature exceeding 1,000° C. also is objectionable, because of the high cost and reduction in the surface area caused by partial fusion of the rare-earth oxide. The time of said activation treatment is not critical, as it varies depending on the amount of surface-adsorbed matter or the treating temperature, but normally it ranges 1–100 hours.

While the shape of the catalyst to be used in the present invention is not critical, it is desirable that the catalyst has been molded to facilitate passage of liquid during the reaction time and separation of the catalyst after the reaction. Thus, the catalyst may be in the form of a fine powder of the size around 100 μm, for example, or may be molded by a method commonly practiced, such as granulation or tablet punching.

In the occasion of preparing the catalyst to be used in the present invention, a suitable binder may also be added. Such a binder is used to increase mechanical strength of the catalyst by binding the rare-earth oxide or oxides. The binder may be inorganic or organic so long as it does not interfere with the reaction of the present invention or impair catalytic activity of rare-earth oxide. Furthermore, it is permissible for the binder to exhibit slight catalytic activity for the reaction. Specific examples of the binder useful for the present invention include silica sol, alumina sol, zirconia sol and organic polymer.

A suitable support may also be used in the preparation of the catalyst. Such a support is used for the purpose of enlarging the surface area of catalyst by dispersing rare-earth oxide on the support surface, or for increasing mechanical strength of the catalyst. The support is subject to no critical limitation so long as it does not interfere with the reaction or impair the catalytic activity of rare-earth oxide. It is permissible for the support to exhibit slight catalytic activity for the reaction. Normally used support is selected from various inorganic carriers and clay minerals. Specific examples of the inorganic carriers include silica, alumina, zirconia, titania, silica-alumina, zirconia-titania, silica-zirconia, alumina-titania, silica-titania and alumina-zirconia. Specific examples of useful clay minerals include kaolinites such as kaolinite, dickite, halloysite, chrysotile, lizardite, amesite, etc; smectites such as montmorillonite, beidelite, saponite, hectrite, sauconite, etc.; micas such as muscovite, palagonite, phlogopite, biotite, lepidolite, etc.; hydrotalcites; and talc.

The ratio between alkylene carbonate and alcohol which are used as the starting materials in the present invention is theoretically 2 in terms of molar ratio, but is subject to no critical limitation and can be varied over a wide range in accordance with individual production process. Because the object reaction is an equilibrium reaction, generally it is preferred to raise the ratio of alcohol to improve conversion of the alkylene carbonate. Thus, normally the molar ratio of alkylene carbonate to alcohol ranges 1–20, more preferably 2–10.

Suitable temperature range of the reaction of this invention varies depending on starting materials or catalyst activity, while generally it is 30°–300° C., more preferably 50°–200° C. In the reaction, the pressure is regulated by the vapor pressure of the reaction liquid, and hence subject to no critical limitation. The pressure little affects the transesterification.

In the present invention, the transesterification system of alkylene carbonate and alcohol in the presence of the catalyst may be either batchwise or continuous, which is subject to no critical limitation.

In the batchwise reaction, the catalyst is used within the range of 0.1–30% by weight, more preferably 1–15% by weight, to the starting materials. Charging the batchwise system reactor with each prescribed amount of the catalyst and starting materials of the present invention and stirring the system at the prescribed temperature to carry out the transesterification, a liquid reaction mixture containing the object dialkyl carbonate is obtained. In that occasion, the reaction time varies depending on the reaction temperature and the amount of the catalyst, but normally the reaction is continued for 0.1 to 100 hours, more preferably from 1 to 30 hours. From so obtained reaction liquid containing the catalyst, the catalyst is readily separable by such means as filtration or centrifugation. From the remaining reaction liquid, dialkyl carbonate, side-produced alkylene glycol, unreacted alkylene carbonate and alcohol can be recovered normally by distillation, or otherwise by such means as extraction or recrystallization.

When the reaction is conducted in continuous system, any one of fixed bed system, fluidized bed system or agitation tank system may be used. Suitable liquid feed conditions are, when expressed in terms of liquid-hourly-space velocity (LHSV) to the catalyst, 0.1–50/hr, more preferably 0.2–10/hr.

According to the process of the present invention, the transesterification to form dialkyl carbonate from alkylene carbonate and alcohol progresses speedily. Because the rare-earth oxide or oxides used as the catalyst are insoluble in the reaction liquid, the reaction liquid and the catalyst are readily separable, and the reduction in the yield due to the reverse reaction, decomposition or polymerization which are caused by residual catalyst during the distillation step as observed with known homogeneous catalysts is effectively prevented. Accordingly, industrially important dialkyl carbonate can be produced with high efficiency. Thus, the contribution of the present invention to industrial development is indeed great.

Hereinafter the invention is explained in further details, referring to working examples and comparative examples, it being understood that the present invention is in no way limited thereby.

In the following Examples, the conversions and yields are determined by the following equations.

Alkylene carbonate conversion (mol %) =

$$\left(1 - \frac{\text{mol number of recovered alkylene carbonate}}{\text{mol number of fed alkylene carbonate}}\right) \times 100$$

Alcohol conversion (mol %) =

$$\left(1 - \frac{\text{mol number of recovered alcohol}}{\text{mol number of fed alcohol}}\right) \times 100$$

Dialkyl carbonate yield (mol %) =

$$\left(\frac{\text{mol number of dialkyl carbonate formed}}{\text{mol number of alkylene carbonate supplied}}\right) \times 100$$

Alkylene glycol yield (mol %) =

$$\left(\frac{\text{mol number of alkylene glycol formed}}{\text{mol number of alkylene carbonate supplied}}\right) \times 100$$

EXAMPLE 1

Yttrium nitrate hexahydrate 95.7 g was dissolved in 1000 g of water, to form an aqueous solution of yttrium nitrate. The solution was heated to 80° C. with stirring, into which 500 g of 25% aqueous ammonia was added dropwisely over 2 hours. Stirring was continued for further 5 hours at 80° C., to form an yttrium hydroxide slurry. The slurry was filtered and washed thoroughly with pure water until pH of the filtrate became neutral. Thus, hydrous yttrium hydroxide was obtained. The yttrium hydroxide was dried in air at 120° C., followed by a sequential calcining in air at 500° C. for 5 hours and in nitrogen at 500° C. for 5 hours. The yttrium oxide whereby obtained was labelled Catalyst (1), which had a specific surface area of 58 m$^2$/g.

An autoclave equipped with a stirrer and a thermometer was charged with 1 mol (88 g) of ethylene carbonate, 2 mols (64 g) of methyl alcohol and Catalyst (1) (15.2 g - 10 wt % of the reaction liquid). The system was heated and subjected to the transesterification at the reaction temperature of 100° C. for 2 hours. The reaction pressure was not controlled. After the reaction terminated the reaction liquid was sampled and analyzed of its composition by high performance liquid chromatography. The results are shown in Table 1.

EXAMPLE 2

Example 1 was repeated except that yttrium nitrate hexahydrate was replaced by 108 g of lanthanum nitrate hexahydrate. Thus a lanthanum oxide was formed, which was labelled Catalyst (2). The Catalyst (2) had a specific surface area of 49 m$^2$/g.

A transesterification was conducted in the identical manner with the reaction in Example 1, except that Catalyst (1) was replaced by Catalyst (2). The results are shown in Table 1.

EXAMPLE 3

Cerium oxide was prepared in the identical manner as in Example 1, except that the yttrium nitrate hexahydrate was replaced by 109 g of cerium nitrate hexahydrate. The product was labelled Catalyst (3), which had a specific surface area of 53 m$^2$/g.

The transesterification was carried out in the identical manner with the reaction in Example 1, except that Catalyst (1) was replaced by Catalyst (3). The results are shown in Table 1.

COMPARATIVE EXAMPLE 1

The transesterification and the analysis of the reaction liquid were carried out in identical manner with those of Example 1, except that a hydrotalcite compound [composition: $Mg_6Al_2(OH)_{16}CO_3 \cdot 4H_2O$] was used as the catalyst. The catalyst had a specific surface area of 88 m$^2$/g. The results of the analysis are shown in Table 1.

TABLE 1

|  | Catalyst | conversion (mol %) | | yield (mol %) | |
| --- | --- | --- | --- | --- | --- |
|  |  | EC | MeOH | EG | DMC |
| Example 1 | yttrium oxide | 59 | 45 | 30 | 32 |

TABLE 1-continued

| | Catalyst | conversion (mol %) EC | MeOH | yield (mol %) EG | DMC |
|---|---|---|---|---|---|
| Example 2 | lanthanum oxide | 58 | 45 | 30 | 32 |
| Example 3 | cerium oxide | 59 | 45 | 30 | 32 |
| Comp. Ex. 1 | hydrotalcite | 45 | 28 | 13 | 14 |

EC: ethylene carbonate
MeOH: methyl alcohol
EG: ethylene glycol
DMC: dimethyl carbonate According to the data in above Table 1, in all of the Examples the reaction liquid reached the state of equilibrium under the specified reaction conditions and the reactions terminated apparently. In contrast, under the same reaction conditions the reaction liquid in Comparative Example 1 failed to yet reach the equilibrium composition, although the catalyst used therein had a specific surface area larger than those of the catalysts used in Examples 1-3.

From this fact it can be understood that the catalysts in Examples 1-3 achieve higher reaction rate and exhibit higher catalytic activity than those of the catalyst in Comparative Example 1.

EXAMPLE 4

Yttrium nitrate hexahydrate 5.08 g was dissolved in 10.8 g of water, to provide an aqueous solution of yttrium nitrate. Fifteen (15.0) g of silica gel (CARIACT-30 ® manufactured by Fuji Devison) was impregnated with the solution prepared as described above and dried in air at 120° C., followed by a sequential calcination in air at 500° C. for 5 hours and in nitrogen at 500° C. for 5 hours. Thus, yttrium oxide supported on silica gel was obtained, which was labelled Catalyst (4). This support type catalyst contained 10 wt % thereof yttrium oxide, and had a specific surface area of 110 $m^2/g$.

Ten (10) ml of Catalyst (4) was filled in a tubular reactor (inner diameter: 10 mm; length: 150 mm). Through said reactor a starting liquid composed of ethylene carbonate/methyl alcohol=½ (mol/mol) was passed by means of a quantitative pump at a space-hourly velocity of 2/hr. Then the pressure was set to be 10 kg/$cm^2$ and the tubular reactor was immersed in an oil bath of 100° C. to initiate the reaction. The reaction liquid was sampled periodically and the composition of the samples was analyzed by high performance liquid chromatography. The results are shown in Table 2 below.

TABLE 2

| Reaction Time (Hr) | Conversion (mol %) EC | MeOH | Yield (mol %) EG | DMC |
|---|---|---|---|---|
| 5 | 59 | 45 | 30 | 32 |
| 100 | 59 | 45 | 30 | 32 |
| 1000 | 59 | 45 | 30 | 32 |

According to the results of Example 4, under the above-specified reaction conditions the composition of the reaction liquid reached an equilibrium state, and even after 1,000 hours' use the catalyst activity showed no deterioration. High durability of this catalyst is thus demonstrated.

EXAMPLE 5

Lanthanum nitrate hexahydrate 2.00 g was dissolved in 7.3 g of water to provide an aqueous solution of lanthanum nitrate. Fifteen (15.0) g of γ-alumina (NEOBEAD GB-45 ® manufactured by Mizusawa Chemical Industries, Co.) was impregnated with the solution prepared as described above and dried in air at 120° C., followed by a sequential calcination in air at 500° C. for 5 hours and in nitrogen at 500° C. for 5 hours. Thus lanthanum oxide supported on γ-alumina was obtained, which was labelled Catalyst (5). This support-type catalyst contained 5 wt % thereof of lanthanum oxide and had a specific surface area of 194 $m^2/g$.

The transesterification and the analysis as in Example 4 were repeated, except that Catalyst (4) was replaced by Catalyst (5). The results are shown in Table 3. According to the data shown in Table 3, it can be understood that Catalyst (5) also has high durability.

TABLE 3

| Reaction Time (Hr) | Conversion (mol %) EC | MeOH | Yield (mol %) EG | DMC |
|---|---|---|---|---|
| 5 | 59 | 45 | 30 | 32 |
| 100 | 59 | 45 | 30 | 32 |
| 1000 | 59 | 45 | 30 | 32 |

EXAMPLE 6

An autoclave equipped with a stirrer and a thermometer was charged with 1 mol (102 g) of propylene carbonate, 1.25 mols (40 g) of methyl alcohol and 7.1 g (5 wt % of the reaction liquid) of Catalyst (1) which was prepared in the manner described in Example 1. The system was heated, and at the reaction temperature of 160° C., the ester-interchange reaction was conducted for 5 hours. The reaction pressure was not controlled.

After termination of the reaction, composition of the reaction liquid was analyzed by high performance liquid chromatography. Consequently, propylene carbonate conversion was found to be 38 mol %; methyl alcohol conversion, 44 mol %, dimethyl carbonate yield, 20 mol %; and propylene glycol yield, 17 mol %.

EXAMPLE 7

Yttrium nitrate hexahydrate 3.82 g and lanthanum nitrate hexahydrate 0.997 g were dissolved in 11.5 g of water to provide an aqueous solution of yttrium nitrate-lanthanum nitrate mixture. Fifteen (15.0) g of silica gel (CARIACT-30 ® manufactured by Fuji Devison) was impregnated with the solution prepared as described above and dried at 120° C. in air, followed by a sequential calcination in air at 500° C. for 5 hours and in nitrogen at 500° C. for 5 hours. Thus, yttrium and lanthanum oxides as supported on the silica gel were obtain. This product was labelled Catalyst (7). This support type catalyst contained 7.5 wt % of yttrium oxide and 2.5 wt % of lanthanum oxide, and had a specific surface area of 110 $m^2/g$.

The transesterification and the analysis as carried out in Example 4 were repeated except that Catalyst (4) was replaced by Catalyst (7). The results are shown in Table 4.

TABLE 4

| Reaction Time (Hr) | Conversion (mol %) EC | MeOH | Yield (mol %) EG | DMC |
|---|---|---|---|---|
| 5 | 59 | 45 | 30 | 32 |
| 100 | 58 | 45 | 30 | 32 |

EXAMPLE 8

Lanthanum nitrate hexahydrate 2.99 g and cerium nitrate hexahydrate 0.95 g were dissolved in 12.5 g of water to provide an aqueous solution of lanthanum nitrate-cerium nitrate mixture. Fifteen (15.0) g of silica gel (CARIACF 30 ® manufactured by Fuji Devison) was impregnated with the solution prepared as described above and dried at 120° C. in air, followed by a sequential calcination in air at 500° C. for 5 hours and in nitrogen at 500° C. for 5 hours. Thus lanthanum and cerium oxides as carried on the silica gel were obtained. The product was labelled Catalyst (8). This support type catalyst contained 7.5 wt % of lanthanum oxide and 2.5 wt % of cerium oxide, and had a specific surface area of 109 m²/g.

The transesterification and the analysis as carried out in Example 4 were repeated except that Catalyst (4) was replaced by Catalyst (8). The results are shown in Table 5.

TABLE 5

| Reaction Time | Conversion (mol %) | | Yield (mol %) | |
|---|---|---|---|---|
| (Hr) | EC | MeOH | EG | DMC |
| 5 | 59 | 45 | 30 | 32 |
| 100 | 58 | 45 | 30 | 32 |

EXAMPLE 9

Preparation of the catalyst as in Example 1 was repeated except that 95.7 g of yttrium nitrate hexahydrate was replaced by 84.8 g of yttrium nitrate hexahydrate and 8.37 g of magnesium nitrate hexahydrate. Thus yttrium oxide partially containing magnesium oxide was obtained, which was labelled Catalyst (9). The catalyst contained 95 wt % of yttrium oxide and 5 wt % of magnesium oxide, and had a specific surface area of 50 m²/g.

The transesterification and the analysis as carried out in Example 1 were repeated, except that Catalyst (1) was replaced by Catalyst (9). The results are shown in Table 6.

EXAMPLE 10

Preparation of the catalyst as in Example 1 was repeated except that 95.7 g of yttrium nitrate hexahydrate was reduced to 84.8 g and 9.68 g of aluminium nitrate hexahydrate was added instead; and that 75 g of 25% aqueous ammonia was used. Thus, yttrium oxide partially containing aluminium oxide was prepared, which was labelled Catalyst (10). This catalyst contained 95 wt % of yttrium oxide and 5 wt % of aluminium oxide, and had a specific surface area of 59 m²/g.

The transesterification and the analysis as carried out in Example 1 were repeated except that Catalyst (1) was replaced by Catalyst (10). The results are shown in Table 6.

TABLE 6

| Catalyst | | conversion (mol %) | | yield (mol %) | |
|---|---|---|---|---|---|
| | | EC | MeOH | EG | DMC |
| Example 9 | yttrium oxide + magnesium oxide | 59 | 45 | 30 | 32 |
| Example 10 | yttrium oxide + aluminum oxide | 59 | 45 | 30 | 32 |

The results of above Examples 9 and 10 indicate that the catalyst activity is maintained when an oxide of an element other than rare-earth elements is contained in yttrium oxide in an amount of around 5%.

EXAMPLE 11

A mixture of rare-earth oxides was prepared in the identical manner with the catalyst preparation of Example 1, using 1000 g of an aqueous solution containing 100 g of a rare-earth chloride mixture (containing the following rare-earth elements in the form of chloride: cerium 50 wt %, lanthanum 25 wt %, praseodymium 5 wt %, and neodymium 20 wt %) instead of the aqueous solution obtained by dissolving 95.7 g of yttrium nitrate hexahydrate in 1000 g of water; and also using 130 g of 25 wt % aqueous ammonia. The finally obtained oxide-mixture was labelled Catalyst (11), which had a specific surface area of 52 m²/g.

Transesterification and the analysis of the reaction liquid as carried out in Example 1 were repeated, except that Catalyst (1) was replaced by Catalyst (11). The results are shown in Table 7. According to the data shown in the same table, it can be understood that the oxide catalyst of mixed rare-earth elements also exhibits excellent catalytic activity equivalent to those of the catalysts of preceding Examples.

TABLE 7

| Catalyst | | conversion (mol %) | | yield (mol %) | |
|---|---|---|---|---|---|
| | | EC | MeOH | EG | DMC |
| Example 11 | oxide of mixed rare-earth elements | 59 | 45 | 30 | 32 |

COMPARATIVE EXAMPLE 2

An ion-exchange resin DIAION PA-308 ® (quaternary ammonium group-containing strongly basic anion-exchange resin, manufactured by Mitsubishi Kasei Corporation) was used as the catalyst, which was dehydrated by heating to 60° C. under reduced pressure, as a preliminary treatment.

The transesterification and the analysis as carried out in Example 4 were repeated, except that Catalyst (4) was replaced by the above ion-exchange resin. The results are shown in Table 8.

TABLE 8

| Reaction Time | Conversion (mol %) | | Yield (mol %) | |
|---|---|---|---|---|
| (Hr) | EC | MeOH | EG | DMC |
| 5 | 59 | 45 | 30 | 32 |
| 100 | 51 | 35 | 19 | 20 |

According to the results indicated in Table 8, at fifth hour of the reaction using the catalyst the reaction liquid had an equilibrium composition, but after 100 hours' use of the catalyst the reaction liquid failed to have an equilibrium composition. This indicates that the catalytic activity decreased with time to reduce the reaction rate, that is, the catalyst has poor durability. In contrast thereto, the catalysts in accordance with the present invention show no decrease in the reaction rate, as demonstrated in Examples 4 or 5, after 1,000 hours use. Thus, it can be understood that the catalysts used in the present invention have high durability.

EXAMPLE 12

An autoclave equipped with a stirrer and a thermometer was charged with 1 mol (90 g) of ethylene carbonate, 2 mols (92 g) of ethyl alcohol and 18.2 g (10 wt % of the reaction liquid) of Catalyst (2) prepared by the method as described in Example 2. The system was heated and subjected to the transesterification at 120° C. for 2 hours. The reaction pressure was not controlled.

After termination of the reaction, the composition of the reaction liquid was analyzed by high performance liquid chromatography. The results were: ethylene carbonate conversion, 57 mol %; ethyl alcohol conversion, 43 mol %; diethyl carbonate yield, 30 mol %; and ethylene glycol yield, 29 mol %.

EXAMPLE 13

The transesterification and the analysis as carried out in Example 4 were repeated, except that a starting material composed of ethylene carbonate/methyl alcohol=1/5 (mol/mol) was used. The results are shown in Table 9 below.

TABLE 9

| Reaction Time (Hr) | Conversion (mol %) | | Yield (mol %) | |
|---|---|---|---|---|
| | EC | MeOH | EG | DMC |
| 5 | 78 | 26 | 54 | 55 |
| 100 | 79 | 26 | 54 | 55 |

According to the data in above Table 9 as well as those in Table 2, the following can be understood: when the ratio of methyl alcohol in the starting composition is increased, in the equilibrium composition of the reaction liquid ethylene carbonate conversion increases, methyl alcohol conversion decreases, and yields of ethylene glycol and dimethyl carbonate increase.

We claim:

1. A process for preparing dialkyl carbonate which comprises subjecting an alkylene carbonate of the formula (1)

$$R^1-\underset{\underset{O}{|}}{\overset{\overset{R^2}{|}}{C}}-\underset{\underset{O}{|}}{\overset{\overset{R^3}{|}}{C}}-R^4, \quad \underset{C}{\underset{\|}{}} \quad (1)$$

in which $R^1$, $R^2$, $R^3$ and $R^4$ each independently is selected from the group consisting of hydrogen atom, alkyl, alkenyl, aryl, cycloalkyl, alkoxyalkyl and alkoxy groups, and an alcohol of the formula (2)

$$R^5 OH \quad (2)$$

in which $R^5$ is selected from the group consisting of $C_1$-$C_{20}$ alkyl, alkenyl, arylalkyl, cycloalkyl or alkoxyalkyl groups, to a transesterification reaction to form a dialkyl carbonate of the formula (3)

$$R^5OCOR^5, \quad (3)$$
$$\underset{O}{\|}$$

in which $R^5$ is the same as defined above, by contacting said alkylene carbonate and said alcohol with a catalyst consisting essentially of rare earth oxide.

2. The process as described in claim 1, in which the rare earth oxide catalyst is at least one of yttrium oxide, lanthanum oxide and cerium oxide.

3. The process as described in claim 1, in which the rare earth oxide catalyst has a specific surface area within a range 10–300 m$^2$/g.

4. The process as described in claim 1, in which the rare earth oxide catalyst is carried on a support.

5. The process as described in claim 1, in which the alkylene carbonate is ethylene carbonate and the alcohol is methyl alcohol.

6. The process of claim 1 in which the rare earth oxide catalyst consists essentially of cerium oxide, lanthanum oxide, praseodymium oxide and neodymium oxide.

7. A process for preparing dialkyl carbonate which comprises subjecting an alkylene carbonate of the formula (1)

$$R^1-\underset{\underset{O}{|}}{\overset{\overset{R^2}{|}}{C}}-\underset{\underset{O}{|}}{\overset{\overset{R^3}{|}}{C}}-R^4, \quad \underset{C}{\underset{\|}{}} \quad (1)$$

in which $R^1$, $R^2$, $R^3$ and $R^4$ each independently is selected from the group consisting of hydrogen atom, alkyl, alkenyl, aryl, cycloalkyl, alkoxyalkyl and alkoxy groups, and an alcohol of the formula (2)

$$R^5 OH \quad (2)$$

in which $R^5$ is selected from the group consisting of $C_1$-$C_{20}$ alkyl, alkenyl, arylalkyl, cycloalkyl or alkoxyalkyl groups, to a transesterification reaction to form a dialkyl carbonate of the formula (3)

$$R^5OCOR^5, \quad (3)$$
$$\underset{O}{\|}$$

in which $R^5$ is the same as defined above, by contacting said alkylene carbonate and said alcohol with a rare earth metal oxide which consists essentially of a member of the group consisting of yttrium oxide, lanthanum oxide, cerium oxide and mixtures thereof.

8. The process of claim 7 wherein said alkylene carbonate is a member selected from the group consisting of ethylene carbonate and propylene carbonate and mixtures thereof.

9. The process of claim 7 wherein said alcohol is a member selected from the group consisting of methyl alcohol and ethyl alcohol and mixtures thereof.

10. The process of claim 7 wherein said rare earth oxide catalyst consists essentially of yttrium oxide.

11. The process of claim 7 wherein said rare earth oxide catalyst consists essentially of cerium oxide.

12. The process of claim 7 wherein said rare earth oxide consists essentially of lanthanum oxide.

13. A process for preparing dialkyl carbonate which comprises subjecting an alkylene carbonate selected from the group consisting of ethylene carbonate and propylene carbonate,
and an alcohol of the formula (2)

$$R^5 OH \tag{2}$$

in which $R^5$ is selected from the group consisting of methyl and ethyl, to a transesterification reaction to form a dialkyl carbonate of the formula (3)

$$R^5OCOR^5, \tag{3}$$
$$\underset{O}{\|}$$

in which $R^5$ is the same as defined above,
by contacting said alkylene carbonate and said alcohol with a rare earth oxide catalyst which consists essentially of a member of the group consisting of yttrium oxide, lanthanum oxide, cerium oxide and mixtures thereof.

14. The process of claim 13 wherein said rare earth oxide catalyst consists essentially of yttruim oxide.

15. The process of claim 13 wherein said rare earth oxide catalyst consists essentially of cerium oxide.

16. The process of claim 13 wherein said rare earth oxide catalyst consists essentially of lanthanum oxide.

17. The process of claim 13 wherein said rare earth oxide catalyst consists essentially of yttrium oxide and lanthanum oxide.

18. The process of claim 13 wherein said rare earth oxide catalyst consists essentially of lanthanum and cerium oxide.

* * * * *